United States Patent [19]

Fernholz et al.

[11] 4,132,733

[45] Jan. 2, 1979

[54] PROCESS FOR THE MANUFACTURE OF AN ADDITION COMPOUND OF SORBIC ACID AND POTASSIUM SORBATE (POTASSIUM DISORBATE)

[75] Inventors: Hans Fernholz, Fischbach; Hans-Joachim Schmidt, Falkenstein; Friedrich Wunder, Flörsheim am Main, all of Fed. Rep. of Germany

[73] Assignee: Hoechst Aktiengesellschaft, Frankfurt am Main, Fed. Rep. of Germany

[21] Appl. No.: 585,603

[22] Filed: Jun. 10, 1975

[30] Foreign Application Priority Data

Jun. 12, 1974 [DE] Fed. Rep. of Germany ....... 2428411

[51] Int. Cl.$^2$ ............................................. C07C 51/52
[52] U.S. Cl. ..................................................... 562/601
[58] Field of Search ................................... 260/526 N

[56] References Cited

U.S. PATENT DOCUMENTS 3,139,378    6/1964    Gooding ........................ 260/526 N Primary Examiner—Vivian Garner
Attorney, Agent, or Firm—Curtis, Morris & Safford

[57] ABSTRACT

Process for the manufacture of a molecular compound of sorbic acid — potassium sorbate by means of crystallization from a solution of sorbic acid and potassium sorbate.

10 Claims, No Drawings

PROCESS FOR THE MANUFACTURE OF AN ADDITION COMPOUND OF SORBIC ACID AND POTASSIUM SORBATE (POTASSIUM DISORBATE)

It is known that sorbic acid produces with potassium sorbate a readily crystallizing molecular compound of the composition $C_6H_8O_2 \cdot C_6H_7O_2K$, which may be called "potassium disorbate" in analogy to sodium diacetate. However, the manufacture of this compound has not been described hitherto. Whilst sorbic acid, potassium sorbate and to a lesser extent also calcium sorbate are extensively used as preservatives by the foodstuff industry, potassium disorbate did not gain any noteworthy importance, although its advantageous use for preserving certain foodstuffs, which are especially sensitive to pH modifications, has been described.

A process for the manufacture of an addition-compound of sorbic acid and potassium sorbate of formula $C_6H_8O_2 \cdot C_6H_7O_2K$ has been found which comprises that a solution is prepared containing from 12 to 40 parts by weight of sorbic acid at a temperature of from 45 to 95° C. per 100 parts by weight of an aqueous 40–58 weight % potassium sorbate solution, that the warm solution is optionally purified by means of an adsorbent and crystallized by cooling to room temperature. The solution of the composition according to the invention can be prepared by dissolving sorbic acid at a temperature of from 45° to 95° C. in potassium sorbate solution. But it is possible as well to blend a sorbic acid solution with such a quantity of potassium hydroxide that the sorbic acid is partially neutralized and a solution is produced with a content of sorbic acid and potassium sorbate as claimed.

An adsorptive purification is advantageous in case that at the base of the process is an unpure or crude sorbic acid or an unpure or crude potassium sorbate. As adsorbents may be taken into consideration the usual porous and surface-active substances such as active coal, boneblack, kieselguhr, bauxite, bentonite as well as adsorption resins. Preference is given to the use of a surface-active coal the preparation of which is based on pit coal containing less than 0.3 weight % of iron.

The warm sorbic acid-potassium sorbate solution may be processed with an adsorbent, e.g. with the active coal prepared from pit coal, continuously or discontinuously. When operating discontinuously, the active coal is advantageously suspended in its finely puverulent form in the hot sorbic acid-potassium sorbate solution and kept in motion by agitation or shaking. On the other hand, the use of a granular active coal is recommended for a continuous processing method. The coal may be set up in that case in a column or in a system comprising several consecutive columns or suitably constructed towers which may be installed either stationary or movable, e.g. as a chute. The sorbic acid-potassium sorbate solution is conveyed through the respective installation either from the bottom to the top or vice-versa or, in case of a chute, in a parallel flow or return-current. As far as the adsorptive purification of the sorbic acid-potassium sorbate solution on an industrial scale is concerned, the continuous processing method is preferred. For this purpose it is most useful to exclude oxygen as far as possible by means of an inert gas atmosphere such as nitrogen.

While the solution, which is optionally purified adsorptively, is cooling off, the adduct of sorbic acid-potassium sorbate crystallizes. The size of the crystals depends essentially on the speed of cooling and agitating. The crystallization product is then separated in the usual manner, e.g. by centrifugation or suction-filtering. Since potassium disorbate is subject to decomposition into its components while being washed with water, the water-soluble potassium sorbate being dissolved and the scarcely water-soluble sorbic acid being retained, an eventual washing process is recommendably carried out with an organic solvent such as acetone. However, it is generally more useful — especially when operating continuously — to dry the product directly without an intermediate washing step, so that a potassium disorbate is obtained which contains approximately 0.1 to 2 weight % of potassium sorbate more-depending on the size of the crystals — than the molar composition of the adduct would normally ihclude. The yield based on the sorbic acid charged in the process, depends essentially on the quantitative proportion of the initial substances. The yield is e.g. from 95% to 99%, if an aqueous solution is prepared which contains from 12 to 20 weight % of sorbic acid and 40 weight % of potassium sorbate.

After having removed the crystallized potassium disorbate, the mother solution containing an excess of potassium sorbate may be re-used practically indefinitely, so that the process according to the invention is very economical. Furthermore, the special advantages of the process as per the invention consist in the facts that it is possible to start from a crude sorbic acid and that the potassium disorbate produced in this way is extremely stable.

The following examples illustrate the invention:

EXAMPLE 1

120 g of sorbic acid are dissolved in a solution of 400 g of potassium sorbate in 480 ml of water, while heating to 80° C. and agitating. After having cooled to room temperature, the crystals are suction-filtered, washed with 100 ml of acetone and dried in a vacuum shelf dryer (20 mm Hg) at 50° C. Yield: 266 g of potassium disorbate (95% calculated on sorbic acid).

EXAMPLE 2

200 g of sorbic acid are dissolved at 80° C. in a solution of 400 g of potassium sorbate in 400 ml of water. After cooling to room temperature, suction-off, washing with acetone and drying in vacuo at 50° C., there are obtained 464 g of potassium disorbate (= 99 %, calculated on sorbic acid).

EXAMPLE 3

25 l of active coal (based on pit coal, granulation: 2–4 mm) which had been freed from iron by sulfuric acid (at 1%) and subsequently neutralized by washing with water, were charged into a tube having a length of 10 m and being equipped with a heating jacket (nominal size: 50 mm) in such a way, that no gas bubbles are formed while charging. At a temperature of from 75°–85° C. a solution prepared at 80° C. of 56 parts by weight of sorbic acid (at 89%), 15.8 parts by weight of potassium hydroxide (scales, at 90%) and of 35.2 parts by weight of water is pumped through this column under a nitrogen atmosphere from the bottom to the top at an hourly rate of 2.5 kg. The purified solution is filtered while still hot and cooled to room temperature within the next 4 hours. The crystallization product is removed by centrifugation and dried in vacuo at 50° C. 1.08 kg of potassium disorbate are obtained per hour, which contains from 0.6–0.7 weight % of potassium sorbate more than the stoichiometric quantity would stand for. The yield is from 98–99%, calculated on the sorbic acid (at 100%). The mother liquor is re-used after dissolution of 22.4 parts by weight of crude sorbic acid and of 5.8 parts by weight of potassium hydroxide in 100 parts by weight of mother liquor.

What is claimed is:

1. A process for the preparation of a sorbic acid-potassium sorbate addition-compound having the formula $C_6H_8O_2 . C_6H_7O_2K$ which comprises heating an aqueous solution containing 12 to 40 parts by weight of sorbic acid per 100 parts by weight of an aqueous solution of 40 to 58 weight percent potassium sorbate to a temperature of 45 to 95° C. to produce a warm solution, cooling the solution to room temperature and crystallizing said sorbic acid-potassium sorbate compound from said solution.

2. The process of claim 1 wherein the aqueous solution is prepared by heating a 40 to 58 weight percent potassium sorbate solution to a temperature of 45 to 95° C. and dissolving 12 to 40 parts by weight of sorbic acid in said solution.

3. The process of claim 1 wherein the aqueous sorbic acid-potassium sorbate solution is prepared by adding potassium hydroxide to a solution of sorbic acid to partially neutralize said sorbic acid.

4. The process of claim 1 wherein said warm solution contains impurities and the impurities are removed from the warm solution by contacting the solution with a porous and surface active adsorbent capable of adsorbing said impurities.

5. The process of claim 4 wherein said adsorbent is a member selected from the group consisting of active coal, boneblack, kieselguhr, bauxite, bentonite and adsorptive resins.

6. The process of claim 4 wherein said adsorbent is an active coal prepared from pit coal.

7. The process of claim 1 wherein the aqueous solution contains 12 to 20 weight percent of sorbic acid and 40 weight percent of potassium sorbate.

8. The process of claim 1 wherein the crystallized sorbic acid-potassium sorbate compound is washed with an organic solvent.

9. The process of claim 8 wherein the crystallized sorbic acid-potassium sorbate compound is washed with acetone.

10. The process of claim 1 wherein the crystallized sorbic acid-potassium sorbate compound is dried directly without a washing step.

* * * * *